(12) United States Patent
Fukumura et al.

(10) Patent No.: US 6,686,509 B2
(45) Date of Patent: Feb. 3, 2004

(54) PROCESS FOR PRODUCING α, α-DIFLUOROCYCLOALKANE COMPOUND

(75) Inventors: Kouki Fukumura, Omuta (JP); Hiroshi Sonoda, Omuta (JP); Hidetoshi Hayashi, Omuta (JP); Masahiko Kusumoto, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 10 days.

(21) Appl. No.: 10/239,654

(22) PCT Filed: Feb. 21, 2002

(86) PCT No.: PCT/JP02/01525

§ 371 (c)(1),
(2), (4) Date: Sep. 24, 2002

(87) PCT Pub. No.: WO02/066409

PCT Pub. Date: Aug. 29, 2002

(65) Prior Publication Data

US 2003/0078460 A1 Apr. 24, 2003

(30) Foreign Application Priority Data

Feb. 22, 2001 (JP) .......................... 2001-045920

(51) Int. Cl.$^7$ .......................... C07C 17/00; C07C 17/08; C07C 19/08

(52) U.S. Cl. .......................... 570/164; 570/165; 570/166; 570/167; 570/168; 570/169

(58) Field of Search .......................... 570/164, 165, 570/166, 167, 168, 169

(56) References Cited

FOREIGN PATENT DOCUMENTS

| | | |
|---|---|---|
| EP | 905109 A1 | 3/1999 |
| JP | 63-48230 A | 2/1988 |
| JP | 63-48278 A | 2/1988 |

*Primary Examiner*—Johann Richter
*Assistant Examiner*—Elvis O. Price
(74) *Attorney, Agent, or Firm*—Burns, Doane, Swecker & Mathis, LLP

(57) ABSTRACT

A method for producing an α,α-difluorocycloalkane at high purity with good efficiency, which comprises a step of treating a fluorocycloalkene with hydrogen fluoride wherein the fluorocycloalkene has one fluorine atom directly bonded to a carbon atom of carbon—carbon unsaturated double bond, more preferably, a step of directly adding the hydrogen fluoride to a reaction mixture obtained by treating the cycloalkanone with the de-oxygen fluorinating agent.

8 Claims, No Drawings

PROCESS FOR PRODUCING α,α-DIFLUOROCYCLOALKANE COMPOUND

TECHNICAL FIELD

The present invention relates to a method for producing an α,α-difluorocycloalkane useful as a raw material for synthesizing medicines, liquid crystal materials and the like.

BACKGROUND ART

Conventionally, as methods for producing an α,α-difluorocycloalkane, there are a method containing a step of reacting a cycloalkanone with sulfur tetrafluoride (e.g., U.S. Pat. No. 2,859,245), a method containing a step of reacting a cycloalkanone with molybdenum hexafluoride (Tetrahedron, (27), 3956 (1971)), a method containing a step of converting a cycloalkanone into a hydrazone derivative before reacting with a halogen fluoride (e.g., J. Am. Chem. Soc. (1987), 109(3), 896), etc. However, these methods use a fluorinating agent which is expensive and has high toxicity and explosiveness, require a special instrument for production, and additionally, show low reaction yield. Therefore, these methods are not admitted as an industrial production method. Further, there is a method containing a step of reacting anhydrous hydrogen fluoride with 1-chlorocyclohexene in the presence or absence of a catalyst (e.g., Helv. Chim. Acta, 46(1963), 1818). However, this method has problems that a complicated procedure is necessary for synthesis of raw materials, and additionally, reaction yield with hydrogen fluoride is not high.

For overcoming these problems, various methods have been recently proposed. For example, Japanese Patent Application Laid-Open (JP-A) No. 63-54331 discloses a step of reacting cyclohexanone with anhydrous trifluoroacetic acid to obtain an acylal compound, and then, reacting it with hydrogen fluoride to obtain 1,1-difluorocyclohexane in high yield under mild conditions. In this method, anhydrous trifluoroacetic acid used in the reaction can be recycled by removing it as trifluoroacetic acid, and then, dehydrating the trifluoroacetic acid with phosphorus pentaoxide and the like. Therefore, the method has a merit of suppressing production cost low. However, the reaction time of the acylal process is very long, and additionally, it is necessary to extract the acylal compound, and then to conduct a fluorinating process. Further, it is necessary to use hydrogen fluoride in large amount ranging from 30 to 50 equivalent, and to use an equipment for recovering hydrogen fluoride. Therefore, the method needs to use a complicated process, and cannot avoid a large equipment load. These points may be large demerits for an industrial method.

As a de-oxygen fluorinating agent for directly obtaining a desired substance from a cycloalkanone, there are methods using aminosulfur trifluoride obtained by deriving from sulfur tetrafluoride (e.g., J. Org. Chem., 40(1975) 574, and JP-A Nos. 11-171858, 9-508646 and 11-505271). In these methods, α,α-difluorocycloalkanes can be synthesized under mild conditions without requiring a special equipment. However, a de-oxygen fluorinating agent used in the methods is expensive. Further, as a large problem, a by-product having a fluorocycloalkene skeleton is produced, and it is extremely difficult to remove the by-product from the desired substance. Therefore, the methods need an enormous labor for the removal.

For example, JP-A No. 11-505271 discloses a method wherein diethylaminosulfur trifluoride (hereinafter, abbreviated as "DAST") is reacted with ethyl 4-cyclohexanonecarboxylate, and then, hydrolysis, neutralization, extraction, drying, de-solvent and distillation under reduced pressure are conducted to obtain ethyl 4,4-difluorocyclohexanecarboxylate in a yield of about 70 to 80% containing ethyl 4-fluoro-3-cyclohexenecarboxylate as an impurity. Further, it discloses a complicated purification procedure as a next step wherein the ethyl 4-fluoro-3-cyclohexenecarboxylate which is a by-product is treated with "OXONE®" and the like. However, such treating process has a problem that it deteriorates the yield of ethyl 4,4-difluorocyclohexanecarboxylate.

JP-A No. 11-171858 discloses a method wherein various aminosulfur trifluorides are reacted with 4-t-butyl-cyclohexanone to obtain 4-t-butyl-1,1-difluorocyclohexane and 4-t-butyl-1-fluorocyclohexene in a production ratio of from 67/33 to 96/4. However, it discloses no specific method for isolating 4-t-butyl-1,1-difluorocyclohexane at a high purity from the mixture thereof.

DISCLOSURE OF INVENTION

The present invention has been accomplished to solve the above-mentioned problems of the prior technologies. Therefore, the object of the present invention is to provide a method capable of producing an α,α-difluorocycloalkane at a higher purity in higher efficiency as compared with conventional methods.

In the prior arts stated above, the by-product having a fluorocycloalkene skeleton has been defined as a merely useless product which should be removed for obtaining an α,α-difluorocycloalkane. However, in variously investigation by the present inventors about a method for efficiently producing an α,α-difluorocycloalkane, they treated a mixture with hydrogen fluoride wherein the mixture contained 1,1-difluorocyclohexane and 1-fluorocyclohexene which was obtained by reacting cyclohexanone with a de-oxygen fluorinating agent such as DAST, and they found that the 1-fluorocyclohexene was easily converted into 1,1-difluorocyclohexane by the treatment. They have further intensively studied based on this knowledge, and resultantly found that 1,1-difluorocyclohexane at a high purity was obtained by directly adding hydrogen fluoride to such reaction mixture, and they completed the present invention.

Namely, the present invention relates to a method for producing an α,α-difluorocycloalkane which comprises a step of treating a fluorocycloalkene with hydrogen fluoride wherein the fluorocycloalkene has one fluorine atom directly bonded to a carbon atom of carbon—carbon unsaturated double bond.

Further, the present invention relates to a method for producing an α,α-difluorocycloalkane which comprises a step of treating a cycloalkanone with a de-oxygen fluorinating agent, and then treating it with hydrogen fluoride.

BEST MODES FOR CARRYING OUT THE INVENTION

In the present invention, the fluorocycloalkene means a cycloalkene having one fluorine atom directly bonded to a carbon atom of carbon—carbon unsaturated double bond.

Listed as the fluorocycloalkenes are, for example, compounds having a 4-membered to 8-membered monocyclic structure, compounds having a condensed ring structure in which adjacent carbon atoms forming a 4-membered to 8-membered monocyclic structure are cross-linked by an alkylene group, compounds having a cyclic structure in which non-adjacent carbon atoms forming a 4-membered to 8-membered monocyclic structure are cross-linked by an alkylene group. Specific examples thereof include fluorocyclobutene, fluorocyclopentene, fluorocyclohexene, fluorocycloheptene, fluorocyclooctene. These fluorocycloalkenes may have a substituent inactive to hydrogen fluoride, at a carbon atom forming a cyclic structure except a carbon atom bonded with fluorine atom. Examples of the substituent, which is inactive to hydrogen fluoride, include alkyl groups such as methyl, ethyl, propyl and butyl; aryl groups, alkoxy groups, halogen atoms, trifluoromethyl group, carboxyl group, alkoxycarbonyl groups, cyano group and nitro group.

Some specific examples of the compounds belonging to fluorocycloalkenes include, 1-fluorocyclobutene, 1-fluoro-2-methylcyclopentene, 1-fluoro-4-methylcycloheptene, 4-t-butyl-1-fluorocyclooctene, 1-fluorocyclohexene, 1-fluoro-2-methylcyclohexene, 1-fluoro-4-methylcyclohexene, 4-t-butyl-1-fluorocyclohexene, ethyl 4-fluoro-3-cyclohexenecarboxylate, 4-fluoro-3-cyclohexenecarboxylic acid, 4-cyano-1-fluorocyclohexene, 4-chloro-1-fluorocyclohexene, 1-fluoro-4-phenylcyclohexene, 1-fluoro-3-phenylcyclohexene, 1-fluoro-4-trifluoromethylcyclohexene, 1-fluoro-3-methoxycyclohexene, 2,6-dimethyl-1-fluorocyclohexene and 1-fluoro-4-nitrocyclohexene.

Fluorocycloalkenes synthesized by any method can be used. For example, it can be used a fluorocycloalkene in a reaction mixture containing an $\alpha,\alpha$-difluorocycloalkane and a fluorocycloalkene wherein the mixture was obtained by treating a cycloalkanone with a de-oxygen fluorinating agent as described later.

In the present invention, an $\alpha,\alpha$-difluorocycloalkane is obtained by treating a fluorocycloalkene with hydrogen fluoride, By this treatment, a fluorine atom of the hydrogen fluoride is bonded to one carbon atom among two carbon atoms of carbon—carbon double bond of the fluorocycloalkene wherein the carbon atom was already directly bonded to a fluorine atom, and a hydrogen atom of the hydrogen fluoride is bonded to the another carbon atom among them wherein the another carbon atom was not bonded to any fluorine atom, and resultantly to produce an $\alpha,\alpha$-difluorocycloalkane. For example, 1,1-difluorocyclohexane can be obtained when the fluorine atom and the hydrogen atom are bonded to carbon—carbon double bond of 1-fluorocyclohexene. Further, 1,1-difluoro-2-methylcyclohexane can be obtained when the fluorine atom and the hydrogen atom are bonded to carbon—carbon double bond of 1-fluoro-2-methylcyclohexene.

As hydrogen fluoride used in this treatment, anhydrous hydrogen fluoride is preferable. However, There is no particular problem even if water exists in a small amount. The amount of hydrogen fluoride is not particularly restricted, and preferably from 1 to 40 mol-fold, particularly preferably from 3 to 30 mol-fold based on the amount of fluorocycloalkene. Use of hydrogen fluoride in an amount of 1 mol or more-fold is preferable from the standpoint of reaction rate etc. Use of hydrogen fluoride in an amount of 40 mol or less-fold is preferable from the economical standpoint because the recovering amount of hydrogen fluoride after the reaction is lowered and the size of a recovering equipment is not increased. After the treatment, the unreacted hydrogen fluoride can be easily recovered by blowing an inert gas such as nitrogen gas into the reaction mixture.

There is no problem whether a solvent is used or not used in the treatment of fluorocycloalkene with hydrogen fluoride. When a solvent is used, the solvent should be not reacted with the hydrogen fluoride nor the fluorocycloalkene. When an aprotic polar solvent is used as the solvent which is not reacted with the hydrogen fluoride nor the fluorocycloalkene, the hydrogen fluoride-treatment can be conducted under an atmospheric pressure or low pressure because the hydrogen fluoride shows high solubility in the aprotic polar solvent. Therefore, when the hydrogen fluoride-treatment is conducted in an industrial scale, it has a large merit to use the aprotic polar solvent because it is unnecessary to use an expensive high pressure equipment having acid resistance.

Listed as the aprotic polar solvent are, for example, ethers such as diethyl ether and tetrahydrofuran; esters such as ethyl acetate and butyl acetate; nitrites such as acetonitrile and propionitrile; amides such as dimethylformamide and dimethylacetamide; urea compounds such as 1,3-dimethyl-2-imidazolidinone and tetramethyl urea.

When a solvent is used in the hydrogen fluoride-treatment, the amount of a solvent used is not particularly restricted and usually from about 0.1 to 10 weight-fold based on reactive raw materials.

Regarding the temperature of hydrogen fluoride-treatment, the suitable range of temperature should be appropriately determined in accordance with the amount of the hydrogen fluoride, use or no-use of the solvent, the amount of the solvent and the like. The temperature is usually from −20 to 120° C., preferably from 0 to 80° C. The temperature of −20° C. or more is preferable in view of the reaction rate and the like. The temperature of 120° C. or less is preferable in view of load on a production equipment and the like.

A Cycloalkanone having at least one hydrogen atom on carbon adjacent to a carbonyl group can be a precursor for the above-mentioned fluorocycloalkene. Namely, the above-mentioned fluorocycloalkene and $\alpha,\alpha$-difluorocycloalkane can be obtained by treating such cycloalkanone with the de-oxygen fluorinating agent. Listed as such cycloalkanones are, for example, compounds having a 4-membered to 8-membered monocyclic structure, compounds having a condensed ring structure in which adjacent carbon atoms forming a 4-membered to 8-membered monocyclic structure are cross-linked by an alkylene group, and compounds having a cyclic structure in which non-adjacent carbon atoms forming a 4-membered to 8-membered monocyclic structure are cross-linked by an alkylene group. Specific examples thereof include cyclobutanones, cyclopentanones, cyclohexanones, cycloheptanones and cyclooctanones.

Specific examples of the above-mentioned cycloalkanones giving fluorocycloalkenes include cyclobutanone, 2-methylcyclopentanone, 4-methylcycloheptanone, 4-t-butyl-cyclooctanone, cyclohexanone, 2-methylcyclohexanone, 4-methylcyclohexanone, 4-t-butylcyclohexanone, ethyl 4-cyclohexanonecarboxylate, 4-cyclohexanonecarboxylic acid, 4-cyanocyclohexanone, 4-chlorocyclohexanone, 4-phenylcyclohexanone, 3-phenylcyclohexanone, 4-trifluoromethyl-cyclohexanone, 3-methoxycyclohexanone, 2,6-dimethylcyclohexanone and 4-nitrocyclohexanone.

There is a tendency that a mixture of $\alpha,\alpha$-difluorocycloalkane and fluorocycloalkene is obtained when the cycloalkanone is treated with the de-oxygen fluorinating agent wherein the cycloalkanone has a chemical structure asymmetric to a line connecting an oxygen atom and a carbon atom in a carbonyl group. For example, when 2-methylcyclohexanone is treated with a de-oxygen fluorinating agent, a mixture is obtained wherein the mixture contains 1-fluoro-2-methylcyclohexene and 1-fluoro-6- methylcyclohexene as fluorocycloalkenes together with 1,1-difluoro-2-methylcyclohexane as an α,α-difluorocycloalkane.

The de-oxygen fluorinating agent used for the treatment of cycloalkanones includes, for example, aminosulfur trifluorides and diaminodifluoromethanes. Listed as the specific examples of the aminosulfur trifluorides are dialkylaminosulfur trifluorides typified by N,N-diethyl-aminosulfur trifluoride (DAST), and modified types thereof, namely, N,N-bis(2-methoxyethyl)aminosulfur trifluoride (Deoxo-fluor: trade name of Air Products Com.), N,N-diarylaminosulfur trifluoride, N-alkyl, N-arylaminosulfur trifluoride. Listed as the specific examples of the diaminodifluoromethanes are bis-dimethyl-amino-difluoromethane, bis-diethylamino-difluoromethane, bis-dipropylamino-difluoromethane, bis-di-i-propyl-amino-difluoromethane, bis-di-n-butylamino-difluoro-methane, bis-di-i-butylamino-difluoromethane, bis-di-t-butylamino-difluoromethane, bis-di-n-pentyl-difluoro-methane, bis-di-n-hexyl-difluoromethane, 2,2-difluoro-1,3-dimethyl-imidazolidine, 2,2-difluoro-1-ethyl-3-methyl-imidazolidine, 2,2-difluoro-1,3-diethyl-imidazol-idine, 2,2-difluoro-1,3-di-n-propyl-imidazolidine, 2,2-difluoro-1,3-di-i-propyl-imidazolidine, 2,2-difluoro-1,3-di-n-butyl-imidazolidine, N-phenyl-N,N,N-trimethyldi-aminodifluoromethane and bis-piperidyl-difluoromethane. Among them, N,N-diethylaminosulfur trifluoride, N,N-bis(2-methoxyethyl)aminosulfur trifluoride and 2,2-difluoro-1,3-dimethyl-imidazolidine are preferable. From the standpoint of easy handling, 2,2-difluoro-1,3-dimethyl-imidazolidine is particularly preferable. The diaminodifluoromethanes can be produced easily, for example, by a method described in JP-A No. 12-038370.

The amount of de-oxygen fluorinating agent used for treating the cycloalkanone is preferably 1 equivalent or more, more preferably from 1 to 5 equivalent based on the raw materials. It is preferable to use the de-oxygen fluorinating agent in an amount of 1 equivalent or more in view of progress of the reaction. It is preferable to use the de-oxygen fluorinating agent in an amount of 5 equivalent or less for the efficiency of reaction per the amount.

There is no problem even if no solvent is used in the reaction of cycloalkanone with de-oxygen fluorinating agent. When a solvent is used, the solvent is not specifically restricted, provided that the solvent is not reacted with the de-oxygen fluorinating agent and the fluorocycloalkene. Examples of preferable solvents include alkanes such as hexane, heptane and cyclohexane; aromatic solvents such as benzene, toluene, xylene and nitrobenzene; halogen-based solvents such as dichloromethane, chloroform and ethylene dichloride; and aprotic polar solvents such as diethyl ether, tetrahydrofuran, glyme, diglyme, acetonitrile, N-methylpyrrolidinone, dimethylformamide, dimethylacetamide and 1,3-dimethyl-2-imidazolidinone.

The temperature of treatment of cycloalkanone with de-oxygen fluorinating agent is preferably from −78° C. to 100° C., more preferably from 0° C. to 80° C., when the de-oxygen fluorinating agent is aminosulfur trifluorides. The treatment at −78° C. or higher is preferable in view of the reaction rate and the like. The treatment at 100° C. or lower is preferable in view of the stability of aminosulfur trifluoride and the like. When the de-oxygen fluorinating agent is diaminodifluoromethane, the temperature of treatment is preferably from 0° C. to 150° C., more preferably from 20° C. to 120° C. The treatment at 0° C. or higher is preferable in view of the reaction rate and the like. The treatment at 150° C. or lower is preferable in view of the stability of diaminodifluoromethane and the like.

The hydrogen fluoride-treatment of a reaction mixture obtained by treating the cycloalkanone with the de-oxygen fluorinating agent can be conducted by the same treatment method under the same reaction conditions as the above-mentioned hydrogen fluoride-treatment of fluorocycloalkene.

Specific examples of the hydrogen fluoride-treatment of fluorocycloalkene or the above-mentioned mixture containing fluorocycloalkene and α,α-difluorocycloalkane include, but not limited to, a method wherein a hydrogen fluoride gas is blown through a gas introduction tube into the fluorocycloalkene or the mixture containing fluorocycloalkene in a reaction vessel, and a method wherein a solution previously prepared by dissolving the hydrogen fluoride in an aprotic polar solvent is added into the fluorocycloalkene or the mixture containing fluorocycloalkene.

When the reaction mixture containing fluorocycloalkene and α,α-difluorocycloalkane obtained by treating the cycloalkanone with the de-oxygen fluorinating agent, it is possible that the de-oxygen fluorinating agent remaining in the reaction mixture is hydrolyzed, then, the fluorocycloalkene or the α,α-difluorocycloalkane or the mixture of them is isolated from the reaction mixture by an operation such as extraction, concentration and distillation, and then the hydrogen fluoride-treatment is conducted. Further, the reaction mixture can be directly treated with the hydrogen fluoride without isolating the fluorocycloalkenes and/or the α,α-difluorocycloalkanes.

Particularly, the method wherein the cycloalkanone is treated with the de-oxygen fluorinating agent, then, without intermediately isolating the fluorocycloalkenes and the α,α-difluorocycloalkanes, hydrogen fluoride is directly added to the reaction mixture containing these compounds, what is called one pot method, needs only a simple procedure, and can be conducted in the same reaction machine. Therefore, this method can simplify a production equipment, and can give a large merit in the case of carrying out in an industrial scale.

As described above, in the present invention, a fluorocycloalkene is treated with hydrogen fluoride, or a cycloalkanone is treated with a de-oxygen fluorinating agent, to obtain a reaction mixture to which hydrogen fluoride is directly added. The reaction mixture produced by this method contains substantially no fluorocycloalkene. Therefore, a special purification process for separating the fluorocycloalkene as conventionally effected is not needed, and the α,α-difluorocycloalkane can be removed easily and in high purity from the reaction mixture by a usual operation such as concentration, extraction and distillation.

The following examples will illustrate the present invention further in detail, but do not limit the scope of the invention. The concentration of 2,2-difluoro-1,3-dimethylimidazolidine (hereinafter, abbreviated as "DFI") in an acetonitrile solution in Synthesis Example 1 was measured according to a high performance liquid chromatography method after deriving DFI by reacting it with aniline. The concentration of a fluorine ion was measured by absorptiometry using a lanthanum-alizarin complexon reagent. Further, fluorocycloalkenes and α,α-difluorocycloalkanes in Synthesis Example 1 and examples were evaluated by quantifying them by an internal standard method according to gas chromatography (hereinafter, abbreviated as "GC").

SYNTHESIS EXAMPLE 1

Synthesis of 2,2-difluoro-1,3-dimethylimidazolidine (DFI):

Into a 500 ml four-necked reaction flask, 80.0 g (0.452 mol) of 2-chloro-1,3-dimethylimidazolinium chloride, 105.1 g (1.810 mol) of potassium fluoride in the form of spray dry article, and 320 ml of acetonitrile were charged, and reacted under a nitrogen atmosphere at 80° C. for 17 hours. The reaction solution was cooled to 25° C., then, an inorganic salt was fractionated from the reaction solution to obtain 414.2 g of an acetonitrile solution of DFI (MW136.14) (DFI concentration in solution: 11.4 wt %, yield: 77%).

This reaction solution was subjected to distillation under reduced pressure, to obtain 32 g of DFI (purity: 98.4%). The physical values are as described below. Boiling point: 47.0° C./37 mmHg, EI-MS: 136 ($M^+$), 117 ($M^+$-$F^+$), IR (neat) $cm^{-1}$: 1486, 1385, 1295, 1242, 1085, 966, F analysis: 27.9% by calculated, 27.7% by measured, $^1$H-NMR (δ, ppm, $CDCl_3$, TMS standard): 2.52 (s, 6H, —$CH_3$×2), 3.05 (s, 4H, —$CH_2CH_2$—), $^{13}$C-NMR (δ, ppm, $CDCl_3$, -45° C., $CDCl_3$ standard): 31.4 (s, —$CH_3$×2), 47.6 (s, —$CH_2CH_2$—), 128.5 (t, J=230 Hz, =$CF_2$), $^{19}$F-NMR (δ, ppm, $CDCl_3$, -45° C., $CFCl_3$ standard): -70.9 (s, =$CF_2$).

EXAMPLE 1

Synthesis of 1,1-difluorocyclohexane (Hereinafter, Abbreviated as "DFC"):

Into a 500 ml glass flask equipped with a stirrer, thermometer, dropping funnel and reflux condenser, 134.60 g (0.979 mol) of 99% DFI and 200 ml of p-xylene were charged, and then 80.07 g (0.808 mol) of 99% cyclohexanone was dropped at 65° C. over 20 minutes while stirring under a nitrogen atmosphere. Thereafter, they were reacted for 8 hours while maintaining the reaction temperature at 80° C., and it was found that the raw material conversion was 90%, the DFC yield was 20%, and the yield of 1-fluorocyclohexene (hereinafter, abbreviated as "FCE") was 68%. After the reaction was completed, the reaction mass separated into two phases, and then the lower phase was separated and removed. The p-xylene phase which was the upper phase was washed with water, and neutralized with saturated sodium bicarbonate water. Further, the p-xylene phase was washed with water twice, and it was dried over sodium sulfate, and it was subjected to distillation to obtain 70.98 g of a mixture of DFC and FCE (16.83 g (0.140 mol) of DFC, 54.03 g (0.540 mol) of FCE).

In a polyethylene bottle containing a magnetic stirrer, 3.0 g of the resulted mixture of DFC and FCE was mixed with a solution prepared previously by blowing 5.6 g (282 mmol) of hydrogen fluoride into 3.2 g of 1,3-dimethyl-2-imidazolidinone (hereinafter, abbreviated as "DMI"). The polyethylene bottle was closely capped, and heated at 50 to 52° C. in a water bath while stirring to effect hydrogen fluoride-treatment for 4 hours. The resulted reaction mass was diluted with 50 ml of ether, and excess amount of hydrogen fluoride was neutralized with sodium bicarbonate water, and the aqueous phase was separated to remain an organic phase, and the organic phase was washed with water, and further dried over magnesium sulfate. Further, the solvent was distilled off under reduced pressure to obtain 2.6 g of DFC (GC purity: 97.8%, no FCE detection, overall yield from cyclohexanone: 63%).

EXAMPLE 2

Synthesis of 4-t-butyl-1,1-difluorocyclohexane (Hereinafter, Abbreviated as "TBDFC"):

Into a 500 ml glass flask equipped with a stirrer, thermometer, dropping funnel and reflux condenser, 27.50 g (0.20 mol) of 99% DFI and 40 ml of toluene were charged. Further, 15.44 g (0.10 mol) of 99% 4-t-butyl-cyclohexanone was dropped at 40° C. over 20 minutes while stirring under a nitrogen atmosphere. Thereafter, they were reacted for 6 hours while maintaining the reaction temperature at 70° C., and it was found that the raw material conversion was 94%, the TBDFC yield was 45%, and the yield of 4-t-butyl-1-fluorocyclohexene (hereinafter, abbreviated as "TBFCE") was 49%. After the reaction was completed, excess amount of DFI was hydrolyzed, and then the lower phase was separated and removed. Further, the toluene phase which was the upper phase was washed with water, and neutralized with saturated sodium bicarbonate water. Further, the toluene phase was washed with water twice, and then it was dried over sodium sulfate, and toluene was distilled off to obtain 15.69 g of a mixture of TBDFC and TBFCE (7.53 g (0.043 mol) of TBDFC, 7.28 g (0.047 mol) of TBFCE).

In a polyethylene bottle containing a magnetic stirrer, 3.00 g of the resulted mixture of TBDFC and TBFCE was mixed with a solution prepared previously by blowing 3.76 g (188 mmol) of hydrogen fluoride into 2.10 g of DMI. This polyethylene bottle was closely capped, and heated at 50 to 52° C. in a water bath while stirring to effect hydrogen fluoride-treatment for 4 hours. The resulted reaction mass was diluted with 50 ml of ether, and excess amount of hydrogen fluoride was neutralized with sodium bicarbonate water, and the aqueous phase was separated to remain an organic phase, and the organic phase was washed with water, and further dried over magnesium sulfate. Further, the solvent was distilled off under reduced pressure to obtain 2.74 g of TBDFC (GC purity: 97.0%, no TBFCE detection, overall yield from 4-t-butyl-cyclohexanone: 81%).

EXAMPLE 3

Synthesis of Ethyl 4,4-difluorocyclohexanecarboxylate (Hereinafter, Abbreviated as "EDFC"):

Into a 200 ml glass flask equipped with a stirrer, thermometer, dropping funnel and reflux condenser, 24.5 g (0.177 mol) of DFI and 60 ml of toluene were charged. Further, 24.9 g (0.146 mol) of ethyl 4-cyclohexanone-carboxylate was dropped at 65° C. over 20 minutes while stirring under a nitrogen atmosphere. Thereafter, they were reacted for 6 hours while maintaining the reaction temperature at 85° C., and it was found that the raw material conversion was 82%, the EDFC yield was 21%, and the yield of ethyl 4-fluoro-3-cyclohexenecarboxylate (hereinafter, abbreviated as "EFEC") was 58%. After the reaction was completed, excess amount of DFI was hydrolyzed under cooling by ice, and then the aqueous phase was separated. The organic phase was washed with saturated sodium bicarbonate water and purified water. Further, the toluene was distilled off under reduced pressure to obtain 22.4 g of a mixture containing 5.8 g of EDFC, 14.1 g of EFEC and 0.1 g of ethyl 4-cyclohexanonecarboxylate.

In a polyethylene bottle containing a magnetic stirrer, 10.3 g of the resulted mixture was mixed with a solution prepared previously by blowing 4.3 g (216 mmol) of hydrogen fluoride into 1.5 g of DMI. This polyethylene bottle was closely capped, and heated at 50 to 52° C. in a water bath while stirring to effect hydrogen fluoride treatment for 4 hours. The resulted reaction mass was diluted with 50 ml of ether, and excess amount of hydrogen fluoride was neutralized with sodium bicarbonate water, and the aqueous phase was separated to remain an organic phase, and the organic phase was washed with water, and further dried over magnesium sulfate. Further, the solvent was distilled off under reduced pressure, and then distillation under reduced pressure was effected to give 8.8 g of pure EDFC (bp: 55 to 67° C./3 to 7 mmHg, GC purity: 100%, no EFEC detection, overall yield from ethyl 4-cyclohexanonecarboxylate: 68%).

EXAMPLE 4

Synthesis of Ethyl 4,4-difluorocyclohexanecarboxylate (EDFC):

Into a 30 ml glass flask equipped with a magnetic stirrer and reflux condenser, 1.02 g (6.0 mmol) of ethyl 4-cyclohexanonecarboxylate and 5 ml of methylene chloride were charged. They were cooled by ice while stirring under a nitrogen atmosphere. Into the reaction vessel, 1.43 g (8.9 mmol) of diethylaminosulfur trifluoride (DAST) was dropped slowly from an injector, and then the ice bath was removed, and they were reacted at room temperature for 19 hours. It was found that the raw material conversion was 87%, the EDFC yield was 57%, and the EFEC yield was 22%. After the reaction was completed, excess amount of DAST was hydrolyzed under cooling by ice, and then the aqueous phase was separated, and the organic phase was washed with saturated sodium bicarbonate water and purified water. Further, methylene chloride was distilled off under reduced pressure to obtain 1.62 g of a mixture containing 0.56 g of EDFC, 0.19 g of EFEC, and 0.11 g of ethyl 4-cyclohexanonecarboxylate.

In a polyethylene bottle containing a magnetic stirrer, 0.91 g of the resulted mixture was mixed with a solution prepared previously by blowing 0.33 g (16 mmol) of hydrogen fluoride into 0.11 g of DMI. The polyethylene bottle was closely capped, and heated at 50 to 52° C. in a water bath while stirring to effect hydrogen fluoride-treatment for 4 hours. The resulted reaction mass was neutralized with sodium bicarbonate water, and then analyzed by GC. It was found that the EDFC yield in the reaction mass was 0.42 g and the GC area ratio of EFEC to EDFC was 0.6% (overall yield from ethyl 4-cyclohexanone-carboxylate: 65%).

EXAMPLE 5

Synthesis of Ethyl 4,4-difluorocyclohexanecarboxylate (EDFC):

Into a 30 ml glass flask equipped with a magnetic stirrer and reflux condenser, 1.03 g (6.0 mmol) of ethyl 4-cyclohexanonecarboxylate and 5 ml of methylene chloride were charged, and then they were cooled by ice while stirring under a nitrogen atmosphere. Into the reaction vessel, 2.10 g (9.5 mmol) of Deoxo-fluor (trade name, manufactured by Air Products com.) was dropped slowly from an injector, and then the ice bath was removed, and they were reacted at room temperature for 19 hours. It was found that the raw material conversion was 89%, the EDFC yield was 56%, and the yield of EFEC was 38%. After the reaction was completed, excess amount of Deoxo-fluor was hydrolyzed under cooling by ice, and then the aqueous phase was separated, and the organic phase was washed with saturated sodium bicarbonate water and purified water. Further, methylene chloride was distilled off under reduced pressure to obtain 1.32 g of a mixture containing 0.54 g of EDFC, 0.33 g of EFEC, and 0.09 g of ethyl 4-cyclohexanonecarboxylate.

In a polyethylene bottle containing a magnetic stirrer, 0.77 g of the resulted mixture was mixed with a solution prepared previously by blowing 0.41 g (21 mmol) of hydrogen fluoride into 0.15 g of DMI. The polyethylene bottle was closely capped, and heated at 50 to 52° C. in a water bath while stirring to effect hydrogen fluoride treatment for 4 hours. The resulted reaction mass was neutralized with sodium bicarbonate water, and then analyzed by GC. It was found that the EDFC yield in the reaction mass was 0.30 g and the GC area ratio of EFEC to EDFC was 0.1% (overall yield from ethyl 4-cyclohexanone-carboxylate: 76%).

EXAMPLE 6

One Pot Synthesis 1 of Ethyl 4,4-difluorocyclohexanecarboxylate (EDFC):

Into a 500 ml polyethylene bottle equipped with a magnetic stirrer, thermometer, dropping funnel, HF blowing tube and exhaust tube, 80.6 g (0.580 mol) of DFI and 120.0 g of toluene were charged. Further, 79.9 g (0.462 mol) of ethyl 4-cyclohexanonecarboxylate was dropped at 70° C. over 1.5 hours while stirring under a nitrogen atmosphere. Thereafter, they were further reacted for 4.5 hours while maintaining the reaction temperature at 70 to 75° C. It was found that the raw material conversion was 86%, the EDFC yield was 22%, and the EFEC yield was 64%. The polyethylene bottle was cooled in an ice bath, and 83.2 g (4.156 mol) of hydrogen fluoride was blown into the reaction mass while stirring over 1 hour. In this procedure, the temperature in the reaction vessel increased from 5° C. to 21° C. After the blowing was stopped, the polyethylene bottle was closely capped, and heated at 50 to 52° C. in a water bath while stirring to effect hydrogen fluoride-treatment for 12 hours. The resulted reaction mass was diluted with 60 g of toluene, and excess amount of DFI was hydrolyzed under cooling by ice, and the aqueous phase was separated. The resulted organic phase was washed with water, neutralized with sodium bicarbonate water, and further washed with water. This organic phase was distilled off under reduced pressure, and distillation under reduced pressure was effected to obtain 64.1 g of pure EDFC (bp: 74 to 77° C./4 to 8 mmHg, GC purity: 99.9%, the EFEC content: 0.1% or less, overall yield from ethyl 4-cyclohexanonecarboxylate: 74%).

EXAMPLE 7

One Pot Synthesis 2 of Ethyl 4,4-difluorocyclohexanecarboxylate (EDFC):

Into a 30 ml Teflon (trade name) bottle equipped with a magnetic stirrer, HF blowing tube and exhaust tube, 2.00 g (11.6 mmol) of ethyl 4-cyclohexanonecarboxylate and 5 ml of diethyl ether were charged, and they were cooled by ice while stirring under a nitrogen atmosphere. Into the reaction vessel, 3.88 g (17.5 mmol) of Deoxo-fluor was dropped slowly from an injector, and then the ice bath was removed, and they were reacted at room temperature for 17 hours. It was found that the raw material conversion was 90%, the EDFC yield was 50%, and the EFEC yield was 40%. After the reaction was completed, the Teflon bottle was cooled in a salt-ice bath, and 2.48 g (123.9 mol) of hydrogen fluoride was blown into the reaction mass while stirring over 4 minutes. After the blowing was stopped, the Teflon bottle was closely capped, and heated at 50 to 52° C. in an oil bath while stirring to effect hydrogen fluoride-treatment for 54 hours. The resulted reaction mass was discharged into ice water and extracted with ether, and then the organic phase was neutralized with sodium bicarbonate water. Further, it was washed with water twice, and then dried over magnesium sulfate, and the ether was distilled off under reduced pressure to obtain 1.79 g of EDFC (GC purity: 98.8%, the EFEC content: 0.1%, overall yield from ethyl 4-cyclohexanonecarboxylate: 80%).

INDUSTRIAL APPLICABILITY

As described above, the fluorocycloalkene, which is a by-product in producing an α,α-difluorocycloalkanes, is defined as a merely useless product which should be removed in the prior arts. In contrast, the fluorocycloalkene, which is a by-product, is converted into an α,α-difluorocycloalkane and it is effectively used in the present invention. Therefore, according to the present invention, an α,α-difluorocycloalkanes at a high purity can be produced with good efficiency by a simpler operation as compared with prior arts. Namely, the present invention is extremely useful as a method capable of industrially producing an α,α-difluorocycloalkane at a high purity and a low cost.

What is claimed is:

1. A method for producing an α,α-difluorocycloalkane which comprises a step of treating a fluorocycloalkene with hydrogen fluoride wherein the fluorocycloalkene has one fluorine atom directly bonded to a carbon atom of carbon—carbon unsaturated double bond.

2. The method for producing an α,α-difluorocycloalkane according to claim 1 wherein the hydrogen fluoride-treatment is conducted in the presence of an aprotic polar solvent.

3. The method for producing an α,α-difluorocycloalkane according to claim 1 wherein the fluorocycloalkene is fluorocyclohexene.

4. The method for producing an α,α-difluorocycloalkane according to claim 1 wherein the fluorocycloalkene is one obtained by treating a cycloalkanone with a de-oxygen fluorinating agent.

5. The method for producing an α,α-difluorocycloalkane according to claim 4 wherein the cycloalkanone is a compound selected from the group consisting of cyclobutanones, cyclopentanones, cyclohexanones, cycloheptanones and cyclooctanones.

6. A method for producing an α,α-difluorocycloalkane which comprises a step of treating a cycloalkanone with a de-oxygen fluorinating agent, and then treating it with hydrogen fluorides.

7. The method for producing an α,α-difluorocycloalkane according to claim 6 wherein the hydrogen fluoride is directly added to a reaction mixture obtained by treating the cycloalkanone with the de-oxygen fluorinating agent.

8. The method for producing an α,α-difluorocycloalkane according to claim 6 wherein the cycloalkanone is a compound selected from the group consisting of cyclobutanones, cyclopentanones, cyclohexanones, cycloheptanones and cyclooctanones.

* * * * *